(12) United States Patent
Sommer et al.

(10) Patent No.: US 7,745,219 B2
(45) Date of Patent: Jun. 29, 2010

(54) REAGENT COMPOSITION FOR THE ANALYSIS OF RESIDUAL WHITE BLOOD CELLS IN LEUKO-REDUCED BLOOD BANKING PRODUCTS

(75) Inventors: Michael J. Sommer, Monroe, NY (US); Pasquale Degiorgio, Yorktown Heights, NY (US); Bronislaw P. Czech, Cortland Manor, NY (US); Gena Fischer, Harrington Park, NJ (US); E. Sabrinah Chapman, Croton-on-Hudson, NY (US); David Zelmanovic, Monsey, NY (US); Jolanta Kunicka, Tarrytown, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1420 days.

(21) Appl. No.: 10/896,338

(22) Filed: Jul. 21, 2004

(65) Prior Publication Data
US 2005/0026240 A1   Feb. 3, 2005

Related U.S. Application Data

(60) Provisional application No. 60/488,945, filed on Jul. 21, 2003.

(51) Int. Cl.
*G01N 33/48* (2006.01)
*G01N 33/49* (2006.01)

(52) U.S. Cl. .............................. 436/2; 436/10; 436/17; 436/63; 436/66

(58) Field of Classification Search .................. 436/2, 436/10, 17, 63, 66
See application file for complete search history.

(56) References Cited

U.S. PATENT DOCUMENTS 5,039,613 A * 8/1991 Matsuda et al. ............... 436/17
5,116,539 A * 5/1992 Hamaguchi et al. ........... 516/77
5,378,633 A * 1/1995 von Behrens et al. ......... 436/63
5,631,165 A * 5/1997 Chupp et al. .................. 436/43
2002/0150907 A1* 10/2002 Fomovskaia et al. .......... 435/6
2002/0182623 A1* 12/2002 Lefevre et al. ................. 435/6

FOREIGN PATENT DOCUMENTS

EP    582736 A1 *  2/1994

OTHER PUBLICATIONS

Pollack et al. 1982. Flow cytometric analysis of RNA content in different cell populations using pyronin Y and methyl green. Cytometry. 3(1):28-35. Abstract only (p. 1).*
Gurevitch et al. 1956. Osmotic Fragility of Human Blood Platelets. Blood. 11(10):924-8.*
Biological Buffers. 2009. Sigma-Aldrich (http://www.sigmaaldrich.com/life-science/metabolomics/bioultra-reagents/biological-buffers.printervie) p. 1-13.*

* cited by examiner

*Primary Examiner*—Taeyoon Kim
(74) *Attorney, Agent, or Firm*—Charles B. Rodman

(57) ABSTRACT

The enumeration and analysis of residual white blood cells in a sample of leukocyte-reduced blood products is conducted by forming a suspension of the leukocyte-reduced blood products with a sufficient amount of a lysing reagent. The lysing reagent comprises a buffer with a low molar concentration, and a non-ionic surfactant. The suspension of leukocyte-reduced blood products and the lysing reagent is incubated for a sufficient time at a temperature sufficient to selectively lyse the platelets and red blood cells without damaging the white blood cells. The white blood cells of the lysed blood products are then contacted with a suitable dye to stain the white blood cells and the number of stained white blood cells is measured. The lysing reagent is free of harsh organic solvents which can damage the plastic components of automated clinical analyzers.

9 Claims, 4 Drawing Sheets

Figure 1. Optical System and Sample Access

Figure 2. LEUKOREDUCTION Analysis

Figure 4. LEUKOREDUCTION Method Linearity: Platelet Products and Platelet Products Spiked with WBCs
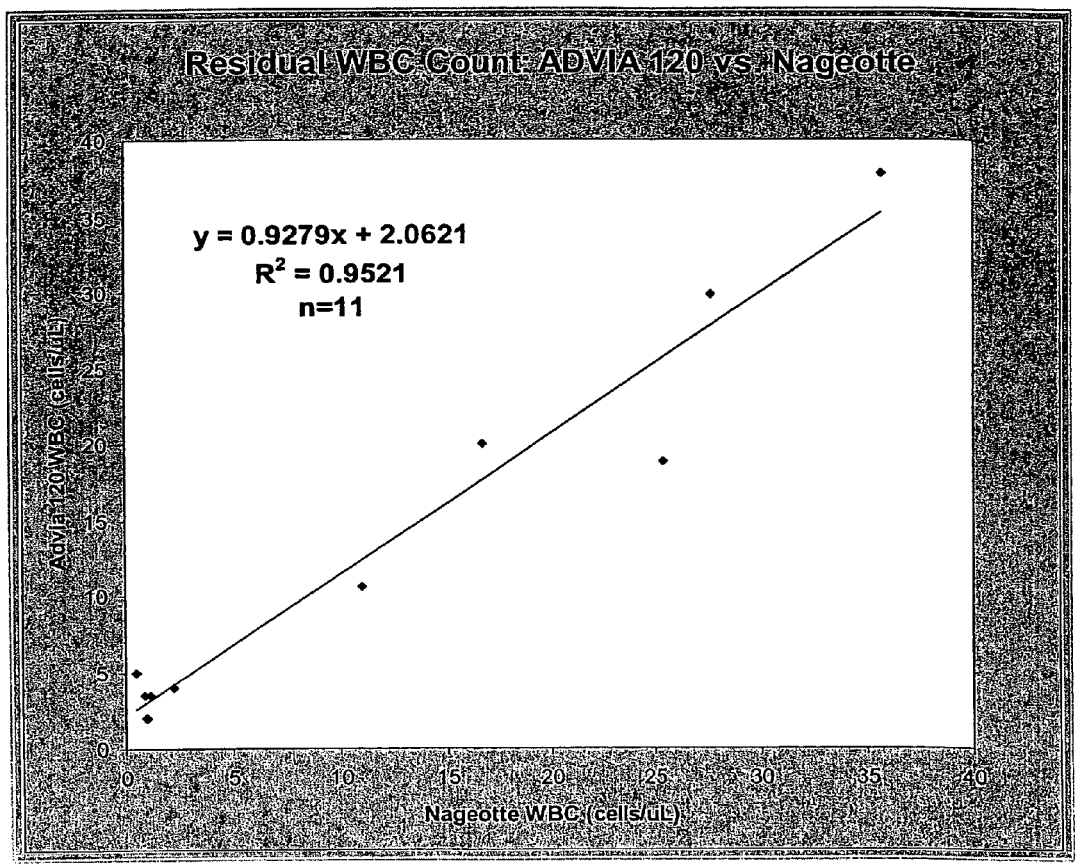

REAGENT COMPOSITION FOR THE ANALYSIS OF RESIDUAL WHITE BLOOD CELLS IN LEUKO-REDUCED BLOOD BANKING PRODUCTS

BACKGROUND OF THE INVENTION

This application claims the benefit of Provisional Application No. 60/488,945 filed Jul. 21, 2003.

This invention relates to the use of a reagent for automated and manual analysis of nucleated cells in suspension, particularly the analysis and enumeration of residual white blood cells or leukocytes with a high degree of accuracy and precision in leuko-reduced blood products including concentrated platelet and packed red blood cell ("RBC") products.

Various methods and systems are known for counting or enumerating the amount of residual white blood cells or leukocytes in blood banking products such as red blood cell concentrates, platelet concentrates, and plasma. Methods for counting the number of residual white blood cells in blood banking products include microscopic examination of manually prepared dilutions of these products in specially designed hemocytometers and flow-cytometric enumeration of white blood cells. (See Moroff et al, "Validation of the Use of the Nageotte Hemocytometer to Count Low Levels of White Cells in White Cell-Reduced Platelet Components" TRANSFUSION, vol. 34, pp. 35-38, (1994), AABB Technical Manual. Method 8.8 "Counting Residual White Cells in Leukocyte-Reduced Blood and Components", Goodfellow et al. "The United Kingdom National External Quality Assessment Scheme Gating and Standardization Strategy for Use in Residual WBC Counting of WBC-Reduced Blood Components", TRANSFUSION, vol. 42, pp. 738-746, (2002), Vachula et al. "A Flow Cytometric Method for Counting Very Low Levels of White Cells in Blood and Blood Components." TRANSFUSION vol. 33, pp. 262-267, (1993).

Current methods for the enumeration of leukocytes use relatively high pHs of about 8.5 and above to facilitate the elimination of the interference of other blood cell-types by differentially lysing these other blood cell types, while leaving a residue of white blood cells for identification and enumeration. The disadvantage of operating at pH's of 8.5 and above is that rapid deterioration of the white blood cells occurs.

Current methods also use harsh organic solvents as leuko-protective agent, including ether/alcohols, such as ethoxyethanol, butoxyethanol, ethoxyethoxyethanol, methoxyethanol, ethyl ether and the like; alcohols, such as isopropyl alcohol dimethyl ethylene glycol, diethylethylene glycol and the like; ketones, such as acetone, methyl ethyl ketone and the like; aprotic solvents, such as dimethyl sulfoxide (DMSO), dimethylformamide (DMF), dimethylacetamide and the like; and furans, such as tetrahydrofuran and the like.

U.S. Pat. No. 4,637,986 to Brown. et al. discloses other leuko-protective agents. The use of such organic solvents is disadvantageous because they can damage or have an adverse effect on the plastic components of automated clinical analyzers operating as flow cytometers. Plastic materials are commonly used in the fabrication of numerous components of automated analyzers including reaction chambers, seals, tubing, waste and storage containers and optical compartments. Chemical solvents that attack these components can render the analytical system inoperable.

Harsh organic solvents that are commonly used as leuko-protective agents can adversely affect the strength, flexibility, surface appearance, color and dimensions of plastic components of automated clinical analyzers. Harsh organic solvents can damage the plastic components of automated clinical analyzers by chemical attack on the plastic polymer chain, such as oxidation and depolymerization, and can cause physical damage when the plastic components absorb the harsh solvents that can result in softening and swelling of the plastic component, permeation of the solvent through the plastic component, and dissolution of the plastic component in a solvent.

Harsh organic solvents include ketones such as acetone or methyl ethyl ketone can dissolve polystyrene and adversely affect low density polyethylene (LDPE) and high density polyethylene (HDPE), polypropylene (PP), neoprene rubbers, acrylates such as Plexiglass™, and Viton™. Ethers, such as ethyl and propyl ethers, can cause swelling, distortion or dissolution of polypropylene, LDPE, HDPE, PP and neoprene rubber. Alcohols can also adversely affect polyethylene. Therefore, use of harsh organic solvents should be avoided.

Automated analysis is more precise than current manual methods for the enumeration of relatively small amounts of leukocytes. The current reference manual analysis method involves introducing a leukocyte-reduced blood sample into a Nageotte hemocytometer. This is a glass slide with small grid on the surface. The sample is introduced to the device and examined under a microscope. Using the grid the white blood cells can be counted.

The total volume of a Nageotte hemocytometer chamber enables about 100 uL of diluted sample to be analyzed. This manual method is time consuming and highly dependent upon operator skill and experience.

In contrast, automated analysis can be adapted to analyze higher sample volumes thus obtaining a better statistical sampling and thereby improve reproducibility and precision of the result. Automation also offers the added advantage of eliminating operator error.

BRIEF DESCRIPTION OF THE DRAWINGS

FIG. 4 is a graphical representation of leukoreduction method linearity.

DESCRIPTION OF THE PREFERRED EMBODIMENTS

Figure 1:
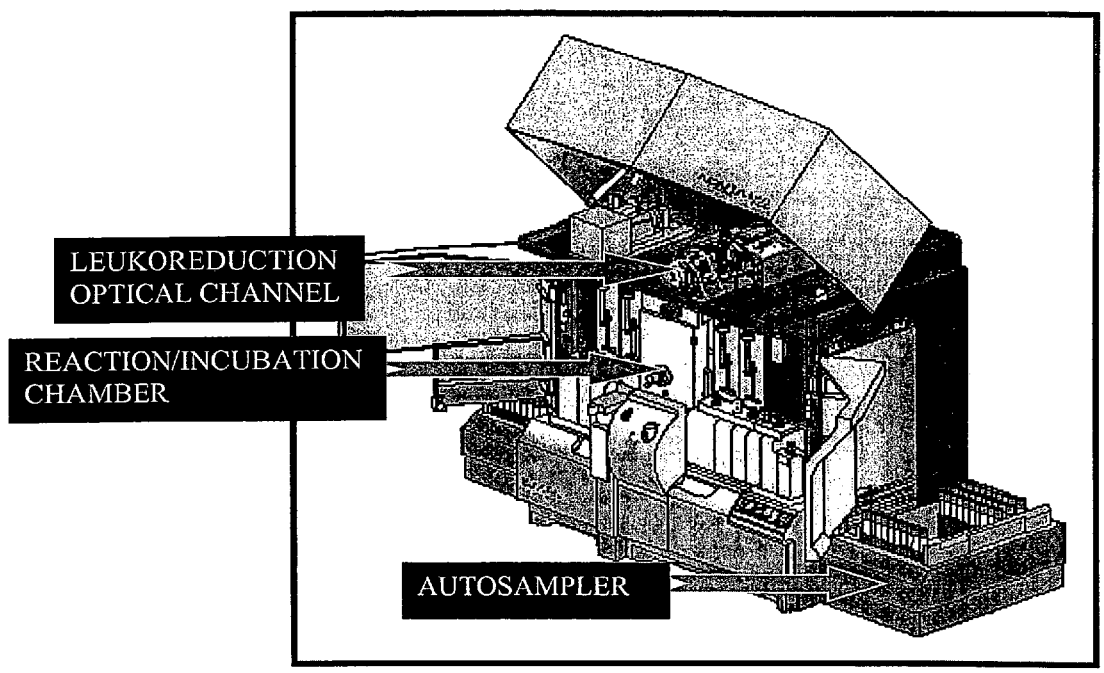
FIG. 1 is a diagrammatic representation of the optical system and sample access.

One embodiment of this invention is the use of the direct cytometry feature of an automated clinical analyzer, such as the Bayer ADVIA 120/2120® Hematology Systems to perform the analysis and enumeration of residual white blood cells in concentrated platelet and packed red blood cell products, and plasma. Direct cytometry as referred to herein, means the direct transfer of an aspirated sample for enumeration and analysis.

Another embodiment of this invention is the use of a novel lysing reagent composition at low pH. The lysing reagent of the present invention contains a non-ionic surfactant, and a buffer prepared at a low molar concentration, and does not contain a harsh organic solvent leuko-protective agent.

The lysing reagent selectively lyses or destroys platelets and red blood cells in suspension in the reagent. This facilitates the analysis and enumeration of residual white blood cells with a high degree of accuracy and precision in leuko-reduced blood banking products such as red blood cells, concentrated platelets, and plasma units.

The analysis of residual white blood cells in leuko-reduced blood products such as packed red blood cells, platelet concentrates, and plasma involves first forming a suspension of the leuko-reduced blood products by contacting or diluting the sample with a sufficient amount of lysing reagent to selectively destroy the platelets and red blood cells in the sample without adversely affecting the white blood cells.

The extent of the dilution or amount of lysing reagent depends on the number of cells in the sample. Cell rich samples would require greater dilution. It has been found that a volumetric ratio of about 2:1 to about 3:1 of lysing reagent to sample, respectively, is sufficient to selectively destroy the platelets and the red blood cells in the sample without adversely affecting the white blood cells. The platelets and red blood cells in the suspension are selectively lysed by the lysing reagent.

It has been discovered that employing the lysing reagent of the present invention, comprising a low ionic-strength buffer and a non-ionic surfactant at a low pH aids in the lysis of red blood cells and platelets while maintaining the integrity of white blood cells without the need for an organic solvent leuko-protective agent.

Buffers are prepared at low molar concentrations with a pH of about 3.5 to about 7.5, preferably about 4.0 to about 7.0 and most preferably at a pH of about 5.5 to about 6.5. The molarity can very from about 2 mM to about 25 mM, preferably about 5 mM to about 15 mM, and most preferably about 6 mM to about 9 mM Preferred buffers include succinic acid (pKa=5.57), citric acid (pKa=5.40), N-2-acetamidoiminodiacetic acid (ADA) (pKa=6.60), 2-(N-morpholino) ethanesulfonic acid (MES) (pKa=6.15) and piperazine-N, N'-bis-(2-ethanesulfonic acid) (PIPES) (pKa=6.80).

A particularly preferred buffer is 2-(N-morpholino) ethanesulfonic acid (MES). MES is preferred because it has a pKa of about 6.15, which is ideal for maintenance of the lysing reagent at a pH of about 6.0 while maintaining a low molar concentration.

The low molar concentration of the lysing reagent helps to establish a hypotonic environment that increases the osmotic gradient. Hypotonic solutions cause water to enter red blood cells thus causing lysis.

The use of non-ionic surfactant or mild detergent is less damaging to the plastic components of analytical instruments commonly used in flow cytometer systems such as the Bayer ADVIA 120/2120® Hematology Systems, than the harsh organic solvents currently being used as leuko-protective agents.

It has also been found that suitable non-ionic surfactants aid in the permeability or penetration of coloring agents, such as dyes, within the nucleus of white blood cell membranes and also may have some role in protecting the leukocytes from lysis.

Suitable non-ionic surfactants are those which do not adversely affect the white blood cells and include Triton X-100™ (Rohm & Haas), an octylphenol polyethylene glycol ether, Tween 20™ (ICI Ltd) a polyoxyethylene sorbitan monolaureate, Tween 80™ (ICI Ltd) a polyoxyethylene sorbitan monooleate, Brij™ (Uniqema) a polyoxyethylene lauryl ether, and the like.

The non-ionic surfactants can vary from about 0.01 weight % to about 1.0 weight % of the lysing reagent, preferably about 0.04 weight % to about 0.50 weight % and most preferably about 0.07% to about 0.25%. The most preferred non-ionic surfactant is Triton X-100™, in amounts which vary from about 0.05 weight % to about 0.5 weight % and preferably about 0.1 weight % to about 0.2 weight % of the lysing reagent.

The lysing reagent also includes about 25 mg/L to about 200 mg/L, preferably about 50 mg/L to about 150 mg/L and most preferably about 75 mg/L to about 125 mg/L of a nucleic acid-specific dye, such as methyl green, methylene blue, pyronin Y, and propidium iodide to differentially stain the DNA or nucleic acids within the nucleus of the white blood cells.

Staining the nuclei of permeabilized white blood cells in lysed blood products with a nucleic acid-specific dye, preferably methyl green or methylene blue, allows the white blood cells to be identified based on their light absorption or light scattering characteristics. Thereafter, the absolute number and concentration of white blood cells can be measured in a suitable manner, such as flow cytometry which enables the white blood cells to be enumerated on an automated basis.

Distinction of the lysed red blood cells and platelets from white blood cells is not necessary because the remnants of the red blood cells and platelets are not stained with the nucleic acid-specific dye. Neither platelets nor red blood cells contain DNA. DNA is the nucleic acid stained by the methyl green or methylene blue dye. The absorbance and/or fluorescence characteristics of the nucleic acid-specific dye make it especially suitable for flow cytometry. The dye makes the white blood cells more prominent and easier to detect by the ADVIA 120/2120® Hematology Systems, by imparting absorbance at a specific wavelength to distinguish the white blood cells from the background. Alternatively, the white blood cells in a prepared sample can be counted manually using a microscope. The manual method is more labor intensive, time consuming and less precise.

The Bayer ADVIA 120/2120® Hematology Systems can perform residual white blood cell analysis and enumeration of blood banking products including but not limited to platelet concentrate and/or packed red blood cell products on an automated basis. The sample can be incubated with the lysing reagent at room temperature for up to about 2 hours, preferably for about 0.5 hours to about 1 hour. The incubated sample of leukocyte-reduced blood products is aspirated through the direct cytomerty feature or hydraulic pathway of the Bayer ADVIA 120/2120® Hematology Systems automated clinical analyzer. Longer incubation times can be used, but are believed to have no beneficial effect.

The specialized analytical features of the Bayer ADVIA 120/2120® Hematology Systems can permit precise analysis of a relatively larger volume of the prepared sample that has undergone lysis compared to the manual method. Manual methods generally allow for only a small sampling of the total white cell population in the original sample. The original sample in the manual method is usually diluted about 1:100 in Turk's Solution, of which 100 uL is counted. The manual method is susceptible to operator and sample handling errors, is less reproducible and less precise than the automated method.

The automated features of the Bayer ADVIA 120/2120® Hematology Systems can calculate the absolute amount of residual white blood cells in counts/μL. If the unit volume of the platelet concentrate and/or packed red blood cell product is provided, the automated Bayer ADVIA 120/2120® Hematology Systems can also calculate the white blood cells in counts/unit.

FIG. 1 is a diagrammatic representation of the optical system and sample access showing the leukoreduction optical channel, the reaction/incubation chamber and auto sampler.

Figure 2:
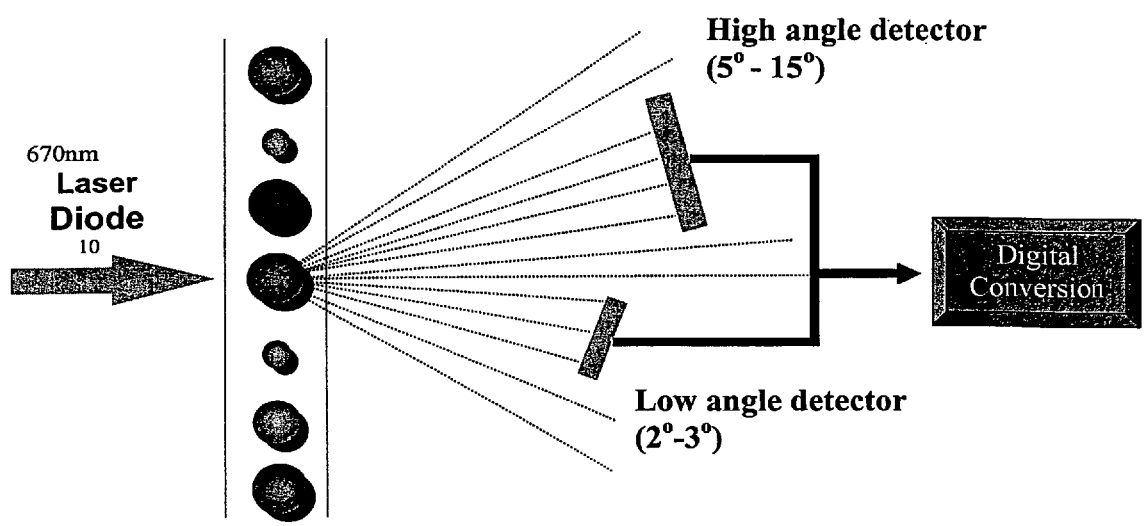
FIG. 2 is a diagrammatic representation of leukoreduction analysis.

FIG. 2 is a diagrammatic representation of the leukoreduction analysis showing the laser diode, high angle detector, and digital conversion.

Figure 3:
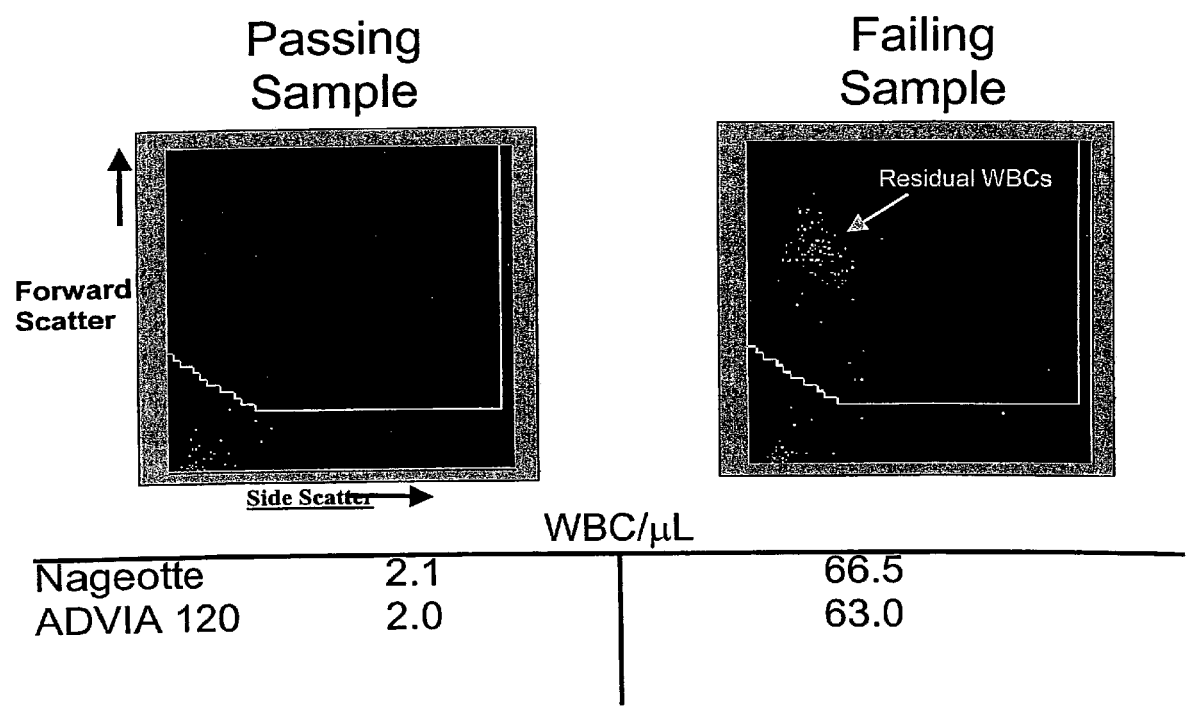
FIG. 3 is a graphical representation of a passing sample and a failing sample.

FIG. 3 is a graphical representation of a passing sample and a failing sample.

FIG. 4 is a graphical representation of the linearity of the leukoreduction method.

Other applications of this invention can include the enumeration of residual white blood cells in other blood banking products, such as platelet concentrates, platelet pheresis, and plasma, packed red cells. In addition, extended or expanded cell counts can be possible in extremely leukopenic whole blood samples.

What is claimed is:

1. An automated clinical analysis method for the enumeration and analysis of residual white blood cells in a sample of leukocyte-reduced blood products selected from the group consisting of plasma, red blood cells, and platelets, consisting essentially of:
   a) forming a suspension of said sample of leukocyte-reduced blood products by contacting said sample with a sufficient amount of a lysing reagent to selectively destroy the platelets and red blood cells in the sample, wherein said lysing reagent consists essentially of:
      i) about 2mM to about 25mM of a buffer selected from the group consisting of succinic acid, citric acid, N-2-acetamidoiminodiacetic acid, 2-(N-morpholino) ethanesulfonic acid, and piperazine-N, N'-bis-(2-ethanesulfonic acid), and
      ii) about 0.01 weight percent to about 1.0 weight percent of at least one non-ionic surfactant selected from the group consisting of octylphenol polyethylene glycol ether, polyethylene sorbitan monolaureate, polyethylene sorbitan monooleate, and polyoxyethylene lauryl ether, wherein the volumetric ratio of lysing reagent to sample of leukocyte-reduced blood products varies from about 2:1 to about 3:1 respectively;
   b) incubating said suspension of leukocyte-reduced blood products and the lysing reagent for a sufficient time at a temperature sufficient to selectively lyse the platelets and red blood cells without damaging the white blood cells;
   c) contacting the white blood cells of the lysed blood products with about 25 mg/L to about 200 mg/L of a nucleic acid specific dye to stain the DNA or nucleic acids within the nucleus of the white blood cells; and
   d) aspirating the stained white blood cells to the direct cytometry feature of an automated clinical analyzer and measuring the number of stained white blood cells, based on their light absorption or light scattering characteristics; wherein said method is conducted at a pH of about 3.5 to about 5.5.

2. The method of claim 1, wherein the non-ionic surfactant is octylphenol ethoxylate.

3. The method of claim 1, wherein the buffer is 2-(N-morpholino) ethanesulfonic acid.

4. The method of claim 1, wherein the nucleic acid specific dye is selected from the group consisting of methyl green, methylene blue, pyronin Y, and propidium iodide.

5. The method of claim 4, wherein the nucleic acid specific dye is selected from the group consisting of methyl green and methylene blue.

6. The method of claim 1, wherein the amount of nucleic acid specific dye varies from about 75 mg/L to about 125 mg/L of lysing reagent.

7. The method of claim 1, wherein the concentration of white blood cells is measured in an automated hematology analyzer operating as a flow cytometer.

8. The method of claim 7, wherein the incubated sample of leukocyte-reduced blood products is aspirated through a direct cytometry hydraulic pathway of an automated hematology analyzer.

9. The method of claim 1, wherein the white blood cells are measured per unit volume of blood in the sample.

* * * * *